(12) United States Patent
Berg et al.

(10) Patent No.: US 10,107,703 B2
(45) Date of Patent: Oct. 23, 2018

(54) METHOD AND PROCESS FOR DETERMINING GAS CONTENT USING TRANSIENT PRESSURE ANALYSIS

(71) Applicant: INFICON GMBH, Bad Ragaz (CH)

(72) Inventors: Christian Berg, Stafa (CH); Martin Wüest, Malans (CH)

(73) Assignee: INFICON GMBH, Bad Ragaz (CH)

( * ) Notice: Subject to any disclaimer, the term of this patent is extended or adjusted under 35 U.S.C. 154(b) by 216 days.

(21) Appl. No.: 14/917,886

(22) PCT Filed: Sep. 9, 2013

(86) PCT No.: PCT/EP2013/068566
§ 371 (c)(1),
(2) Date: Mar. 9, 2016

(87) PCT Pub. No.: WO2015/032443
PCT Pub. Date: Mar. 12, 2015

(65) Prior Publication Data
US 2016/0223421 A1   Aug. 4, 2016

(51) Int. Cl.
| | |
|---|---|
| G01L 21/02 | (2006.01) |
| G01L 9/12 | (2006.01) |
| G01L 21/00 | (2006.01) |
| G01N 33/00 | (2006.01) |

(52) U.S. Cl.
CPC ............... *G01L 21/02* (2013.01); *G01L 9/12* (2013.01); *G01L 21/00* (2013.01); *G01N 33/0062* (2013.01)

(58) Field of Classification Search
CPC ........... G01L 21/02; G01L 9/12; G01L 21/00; G01N 33/0062

USPC .......................................................... 73/37
See application file for complete search history.

(56) References Cited

U.S. PATENT DOCUMENTS

| | | | | |
|---|---|---|---|---|
| 2,784,373 | A | * 3/1957 | Lawrance | G01M 3/329 324/461 |
| 2001/0006003 | A1 | * 7/2001 | Lehmann | G01M 3/3281 73/49.3 |
| 2006/0250144 | A1 | * 11/2006 | Braun | G01R 27/2605 324/678 |
| 2008/0110008 | A1 | * 5/2008 | Walchli | G01L 9/0079 29/407.08 |

FOREIGN PATENT DOCUMENTS

DE   19651487   6/1998

OTHER PUBLICATIONS

International Preliminary Report on Patentability—PCT/EP2013/068566—dated Mar. 4, 2016. 7 pages.
International Search Report and Written Opinion for PCT App No. PCT/EP2013/068566 dated Jul. 25, 2014, 11 pgs.

(Continued)

*Primary Examiner* — Natalie Huls
*Assistant Examiner* — Monica S Young
(74) *Attorney, Agent, or Firm* — Procopio, Cory, Hargreaves & Savitch LLP

(57) ABSTRACT

A pressure step is applied to the interior of a compartment. A sensor which measures the pressure within compartment, in response of the prevailing pressure level, and the transient step response oscillation frequency is used to identify the gas or gas mixture present in the compartment.

28 Claims, 9 Drawing Sheets

(56) References Cited

OTHER PUBLICATIONS

Choi, I-M, et al., Frequency Analysis of a Step Dynamic Pressure Calibrator, Review of Scientific Instruments, 2013, 83, 6pgs.
Pons, P., et al., Transient Response of Capacitive Pressure Sensors, Sensors and Actuators A, 1992, 32, pp. 616-621.

* cited by examiner

METHOD AND PROCESS FOR DETERMINING GAS CONTENT USING TRANSIENT PRESSURE ANALYSIS

FIELD OF INVENTION

The present invention is directed on a method of measuring a pressure, thereby especially vacuum pressure, of a gas or gas mixture in a compartment.

SUMMARY

It is an object of the present invention to improve such method and apparatus.

This is achieved by the method of measuring pressure, especially vacuum pressure, of a gas or a gas mixture in a compartment of predetermined geometry of inner space, which comprises measuring the pressure by a pressure sensor. At least one step of pressure is applied to the compartment, and the transient step response oscillation frequency—fTSR—is monitored by the addressed pressure sensor in the compartment. The result of monitoring is considered as indicative of the gas or gas mixture in the compartment. The measuring of the addressed pressure by the pressure sensor lasts longer than the transient step response, which means that the more or less stationary pressure level in the compartment before and/or after applying the pressure step, is measured as e.g. for controlling a process which is performed in the compartment at a desired pressure level.

In an embodiment of the method according to the invention, which may be combined with any embodiment thereof still to be addressed, unless in contradiction, applying of the at least one step of pressure comprises applying a pressure step from ambient pressure to a target pressure, preferably to a target vacuum pressure.

In a further embodiment of the method, which may be combined with any of the preaddressed embodiments and with any embodiment still to be addressed, unless in contradiction, applying the at least one step of pressure comprises applying a pressure step from a pressure in the compartment, preferably a vacuum pressure, to ambient pressure.

In an embodiment of the method, which may be combined with any of the preaddressed embodiments as well as with any embodiment still to be addressed, unless in contradiction, applying the at least one pressure step is performed by abruptly expanding a gas from the compartment or into the compartment.

In a further embodiment of the method according to the invention, which may be combined with any of the preaddressed embodiments and with any of the embodiments still to be addressed, unless in contradiction, monitoring the fTSR is performed in time domain or in frequency domain.

In a further embodiment of the method, which may be combined with any of the embodiments of the method already addressed as well as with any embodiment still to be addressed, unless in contradiction, at least one reference fTSR signal indicative for a fTSR of at least one gas or gas mixture is provided.

A signal which depends from the fTSR as monitored is compared with the addressed at least one reference fTSR signal.

In an embodiment of the just addressed embodiment there is provided a multitude of gas or gas mixture specific reference fTSR signals, preferably in form of a look-up table. The signal dependent from the fTSR as monitored by the pressure sensor is compared with the reference fTSR signals. Thereby, a signal is output which is indicative for a gas or gas mixture, the reference fTSR signal thereof fitting best with the signal dependent from the fTSR as monitored.

In an embodiment of the method according to the invention, which may be combined with any of the preaddressed embodiments and embodiments still to be addressed, unless in contradiction, the at least one reference fTSR signal is provided by providing a reference compartment of predetermined geometry of inner space and applying to the reference compartment at least one reference step of pressure, monitoring by a further pressure sensor the resulting fTSR and storing a signal dependent from the addressed resulting fTSR occurring in the reference compartment, as reference fTSR signal.

In an embodiment of the just addressed embodiment the dependent signal stored is derived from the resulting fTSR as a function of at least one of:
   a difference of predetermined geometries of the compartment and of the reference compartment, if at all existing and if relevant and not neglectable;
   a difference of pressure levels at which the fTSR in the reference compartment and in the compartment are monitored, if at all existing and if relevant and not neglectable;
   a difference of temperatures, at which the fTSR are monitored in the reference compartment and in the compartment, if at all existing and if relevant and not neglectable.

A further embodiment, which may be combined with any of the embodiments already addressed and still to be addressed, unless in contradiction, comprises deriving the signal dependent from the fTSR as monitored as a function of at least one of
   a difference of predetermined geometries of the compartment and of the reference compartment, if at all existing and if relevant and not neglectable;
   a difference of pressure levels at which the fTSR in the reference compartment and in the compartment are monitored, if at all existing and if relevant and not neglectable;
   a difference of temperatures, at which the fTSR in the reference compartment and in the compartment are monitored, if at all existing and if relevant and not neglectable.

In one embodiment of the method according to the invention, which may be combined with any of the preaddressed embodiments and embodiments still to be addressed, unless in contradiction, the geometry of the reference compartment is equal to the geometry of the compartment or the reference compartment is realized by the compartment.

In a further embodiment of the method, which may be combined with any of the preaddressed embodiments and any embodiment still to be addressed, unless in contradiction, the further pressure sensor is selected to be equal to the pressure sensor for measuring and monitoring or the further pressure sensor is realized by the addressed pressure sensor.

In a further embodiment of the method which may be combined with any of the preaddressed embodiments and embodiments still to be addressed, unless in contradiction, there is valid at least one of:
   The step of reference pressure is equal to the step of pressure as applied to the compartment to be monitored and measured, The pressure level in the reference compartment before the reference step is applied is equal to the pressure level in the compartment before, the step is applied there.

The stationary pressure level in the reference compartment after the reference step is applied is equal to the stationary pressure level in the compartment after the pressure step is applied there.

The temperature in the reference compartment during applying the reference step is equal to the temperature in the compartment during the pressure step being applied there.

In a further embodiment of the method, which may be combined with any of the preaddressed embodiments and embodiments still to be addressed, unless in contradiction, at least monitoring by the sensor comprises sampling a signal dependent from an output signal of the sensor at a sampling frequency which is at least 5 times, preferably at least 10 times higher than the fTSR, the sampling frequency being at least 0.5 kHz, and even more preferred at least 5 kHz.

Besides of monitoring also the addressed measuring may, and normally is performed by the addressed sampling.

In a further embodiment of the method according to the invention, which may be combined with any of the preaddressed embodiments and any embodiment still to be addressed, unless in contradiction, measuring and monitoring by the pressure sensor comprises Providing a pressure sensing capacitor with two electrodes, the capacity of the capacitor being dependent from pressure in the compartment and electrically monitoring the course of the capacity of the addressed capacitor.

In an embodiment of the just addressed embodiment the course of the addressed capacity is monitored by sampling, whereby each sampling step comprises charging and discharging the capacitor, thereby performing at least one of charging and of discharging of the capacitor via a resistive element of predetermined resistivity. The addressed resistive element is thereby, together with the addressed capacity, decisive for the time course of the at least one of charging and of discharging. A timespan during the at least one of charging and of discharging the capacitor is measured, between a first predetermined charging level and a second different predetermined charging level of the addressed capacitor.

In an embodiment of the just addressed embodiment of the method, measuring of the timespan is performed by Time to Digital Conversion (TDC), e.g. as addressed in the U.S. Ser. No. 07/403,020 B2.

In a further embodiment of the method addressing applying a pressure sensing capacitor, one of the electrodes comprises a ceramic material membrane, preferably made of $Al_2O_3$.

In a further embodiment of the method according to the invention digital signal processing is applied.

The apparatus according to the present invention for measuring pressure, especially a vacuum pressure, in a compartment exposed to a pressure step, comprises:

measuring means for measuring an average pressure level in the compartment, averaged over a predetermined timespan and for generating a respective pressure level indicative signal;

monitoring means for monitoring transient pressure step response oscillation frequency—fTSR—of the pressure in the compartment;

evaluation means for evaluating the fTSR.

In an embodiment of the apparatus according to the invention, which may be combined with any embodiment of the apparatus still to be addressed, unless in contradiction, the measuring means and the monitoring means comprise a common capacitance pressure sensor with a capacitor, the capacity thereof being dependent from an input pressure to be sensed. They further comprise charging/discharging means for charging and discharging the capacitor, whereby at least one of charging and of discharging is performed through a resistive element, the resistivity thereof defining, together with the capacity of the addressed capacitor, the time course of the at least one of charging and of discharging. They further comprise a time measuring means for measuring a timespan, characteristic of the at least one of the charging and of the discharging through the resistive element.

Please note that the resistive element needs not be a discrete resistor, but may be realized e.g. by the resistivity of an electronic switch in conducting state or by a connecting wire etc.

In an embodiment of the just addressed embodiment of the apparatus, it comprises a clock unit which controls charging and discharging at a repetition frequency, which is at least 5 times, preferably at least 10 times higher than an expected fTSR, whereby the addressed repetition frequency, also called sampling frequency, is set to be preferably at least 0.5 kHz and even more preferred at least 5 kHz.

In a further embodiment of the apparatus the addressed time measuring means comprise a Time to Digital Converter (TDC).

In a further embodiment of the apparatus, which may be combined with any of the preaddressed embodiments and embodiments still to be addressed, unless in contradiction, the evaluation means comprise a digital signal processing unit, e.g. in the form of a ASIC.

In a further embodiment of the apparatus according to the invention, which may be combined with any of the preaddressed embodiments and embodiments still to be addressed, unless in contradiction, the measuring means and the monitoring means comprise a common pressure sensor, whereby at least the monitoring means comprise sampling means for sampling the output signal of the common pressure sensor at a sampling frequency which is at least 5 times, preferably at least 10 times higher than an expected fTSR. The sampling frequency is thereby preferably set to at least 0.5 kHz, and even more preferred to at least 5 kHz.

In an embodiment of the apparatus according to the invention, which may be combined with any of the preaddressed embodiments and embodiments still to be addressed, unless in contradiction, the measuring means and the monitoring means comprise a common capacitor pressure sensor with a capacitor, the capacity thereof being dependent from an input pressure, the capacitor comprising a membrane electrode of a ceramic material, preferably made of $Al_2O_3$.

In a further embodiment of the apparatus according to the invention, which may be combined with any of the preaddressed embodiments and embodiments still to be addressed, unless in contradiction, the evaluation means comprise comparing means for comparing a signal representing the fTSR with a signal representing a reference fTSR.

In a further embodiment of the apparatus according to the invention, which may be combined with any of the preaddressed embodiments and embodiments still to be addressed, unless in contradiction, the evaluation means comprise a look-up table with a multitude of signals each representing a gas or gas mixture indicative reference fTSR and the comparing means are adapted for comparing a signal representing the fTSR as monitored with the multitude of signals representing the gas or gas mixture indicative reference fTSR. The comparing means are further adapted to output an output signal indicative for at least one specific gas or gas mixture, the signal representing the reference fTSR of the addressed at least one gas or gas mixture fitting best with the signal which represents the fTSR as monitored.

BRIEF DESCRIPTION OF DRAWINGS

The invention shall now be further described and exemplified with the help of figures. The figures show.

DETAILED DESCRIPTION

Figure 1:
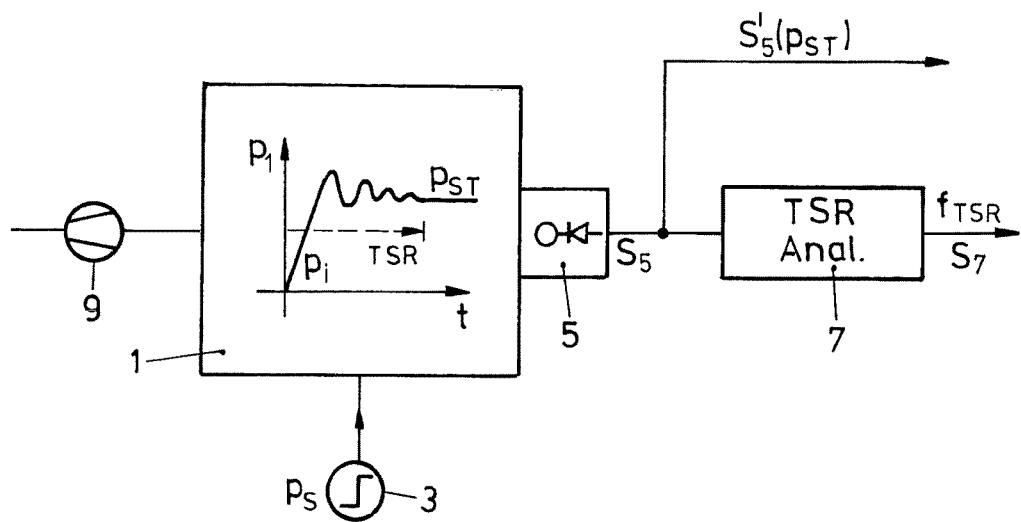
FIG. 1 simplified and schematically by means of a signal flow/functional block diagram, an embodiment of the apparatus according to the invention and operating the method of the invention.

FIG. 1 shows in a most simplified and schematic signal flow/functional block diagram the principle of the method and apparatus according to the present invention in one embodiment. A compartment 1 with a known geometry of its inner space is loaded by a pressure step source 3. The pressure step source 3 generates a pressure step $p_s$ with a slope which is as steep as possible. The pressure $p_1$ in the compartment 1 changes from an initial pressure value $p_i$ to stationary pressure $p_{ST}$ level. Thereby, the pressure step response of $p_1$ in compartment 1 comprises a damped oscillation, the frequency of which being the transient step response oscillation frequency also addressed by fTSR. The transient step response TSR is qualitatively shown in FIG. 1. The pressure in compartment 1 is measured and monitored by means of a pressure sensor 5. The output signal $S_5$ of pressure sensor 5 pictures the pressure $p_1$ prevailing in compartment 1 and thus also the transient step response TSR with the fTSR, besides of the stationary pressure levels $p_i$ and $p_{ST}$.

A signal dependent from the output signal $S_5$ of pressure sensor 5 is input to a TSR analyzer unit 7 which outputs a signal $S_7$ which is indicative for the fTSR. Additionally, the output signal $S_5$ is exploited, as schematically shown by $S'_5$ ($p_{ST}$) for measuring the stationary pressure in compartment 1, which may be the pressure prevailing in compartment 1 before the pressure step $p_s$ is applied, according to FIG. 1 according to $p_i$ and/or the pressure prevailing in the compartment 1 after applying of the pressure step, $p_{ST}$, more generically any stationary pressure in compartment 1 prevailing before and/or after applying the pressure step $p_s$. In view of the TSR these stationary or quasi-stationary pressure levels may be considered as average pressure values, averaged over predetermined timespans. The fTSR is dependent from the gas or gas mixture in compartment 1.

This fTSR is further dependent from the parameter geometry of the inner space of compartment 1 as well as, to a relevant or to a neglectable extent, from the initial pressure level $p_i$, at which the pressure step $p_s$ initiates, the pressure level at which the pressure step $p_s$ terminates as well as from the temperature prevailing in the gas or gas mixture within compartment 1. The output signal of TSR analyzer unit 7 is exploited as an indicative signal for the gas or gas mixture in compartment 1 at the moment pressure step $p_s$ is applied.

The fTSR is indicative for the gas or gas mixture in compartment 1, because it depends from sound velocity in compartment 1, which latter is dependent from gas species or gas mixture species.

Whereas the inventors of the present invention have up to now investigated on pressure step responses when applying a step with an initial pressure $p_i$ being a vacuum pressure and wherein the stationary step response pressure $p_{ST}$ is ambient pressure or inversely, it is believed that the invention may be realized on any initial pressure level $p_i$ and any stationary step response level $p_{ST}$ if the addressed slope of the applied pressure step $p_s$ is fast or steep enough.

Customarily the container 1 will be a compartment which is to be operated on a pressure level which is stationary. This to operate practical processes as e.g. vacuum process, e.g. vacuum coating or vacuum etching processes during respectively needed operation times. Thus, at least one of the initial pressure $p_i$ and of the stationary step response pressure level $p_{ST}$ will have to be stationarily upheld during such processing. To do so customarily there is provided a pressure source, for vacuum pressure levels a vacuum pump, acting on compartment 1 as shown in FIG. 1 by pump 9. Normally, such a pump 9 will not be capable to apply to the compartment 1 a pressure step with a fast enough slope to cause in the transient step response oscillation with fTSR to be evaluated.

FIGS. 2a to 2d show qualitatively different possibilities to apply the pressure step $p_s$ and to apply to compartment 1 a stationary pressure as necessitated e.g. by a practical processing in compartment 1. According to FIG. 2(a) the initial pressure $p_i$, which may be generically spoken on any non-vanishing absolute pressure level, is lowered by the pressure step $p_s$ by means of the pressure step source 3 as of FIG. 1 to achieve a stationary pressure level $p_{ST}$. Afterwards, the pump 9 of FIG. 1 is operated to bring the pressure $p_1$ within compartment 1 to a desired lower pressure level $p_{STp}$ or, as shown in dashed line, to a desired higher pressure level. Thereby, it becomes evident that in fact the pressure which is stationarily exploited in compartment 1 may be established independently from pressure step $p_s$.

According to FIG. 2(b) the pressure step $p_s$ is selected so that, by the step, at least substantially the desired stationary pressure level $p_{ST2}$ is reached, which nevertheless may be stabilized and controlled by action of a pump 9 as shown in FIG. 1.

The course qualitatively shown in FIG. 2(c) accords with the pressure course of FIG. 2(a) with the sole difference that the pressure change direction by the pressure step $p_s$ is inversed. The pressure course qualitatively shown in FIG. 2(d) accords with that of FIG. 2(b) with the sole difference that the pressure change direction of step $p_s$ is inversed.

With an eye on FIG. 1, and there especially on TSR analyzer unit 7, the analyzing operation therein may be performed in time domain or in frequency domain, i.e. analyzing the frequency spectrum of signal $S_5$ to determine fTSR. Clearly, in latter case the output signal of sensor 5 is time domain to frequency domain converted as by FFT (fast fourier transform) as perfectly known to the skilled artisan.

With an eye on the fact that the fTSR as monitored and identified by signal $S_7$, is indicative for a gas or gas mixture or at least for a group of gases or gas mixtures, one may in an embodiment detect by the addressed processing a difference of gas or gas mixture prevailing on one hand in compartment 1 at one moment, and on the other hand at a different moment. Thereby, e.g. leakiness of the compartment 1 over long operating times may be detected. Such processing is addressed in FIG. 3 qualitatively showing in analogy to the representations in FIG. 2 the course of pressure $p_1$ in compartment 1. Departing from a first initial pressure $p_{i1}$ a first pressure step $p_{s1}$ is applied, establishing a first step response stationary pressure level $p_{ST1}$. Thereafter, with or without changing the pressure $p_{ST1}$ in compartment 1 by a pump, as of pump 9 of FIG. 1, and according to the pressure courses represented in FIG. 2, the compartment 1 is exploited for practical processing. At the end of such processing the then prevailing pressure in compartment 1 is exploited as second initial pressure $p_{i2}$ and there is applied a second pressure step $p_{s2}$. The difference between fTSR$_1$ for $p_{s1}$ and FTSR$_2$ for $p_{s2}$, ΔfTSR indicates generically that the gas or gas mixture in compartment 1 has changed during processing.

Figure 2:
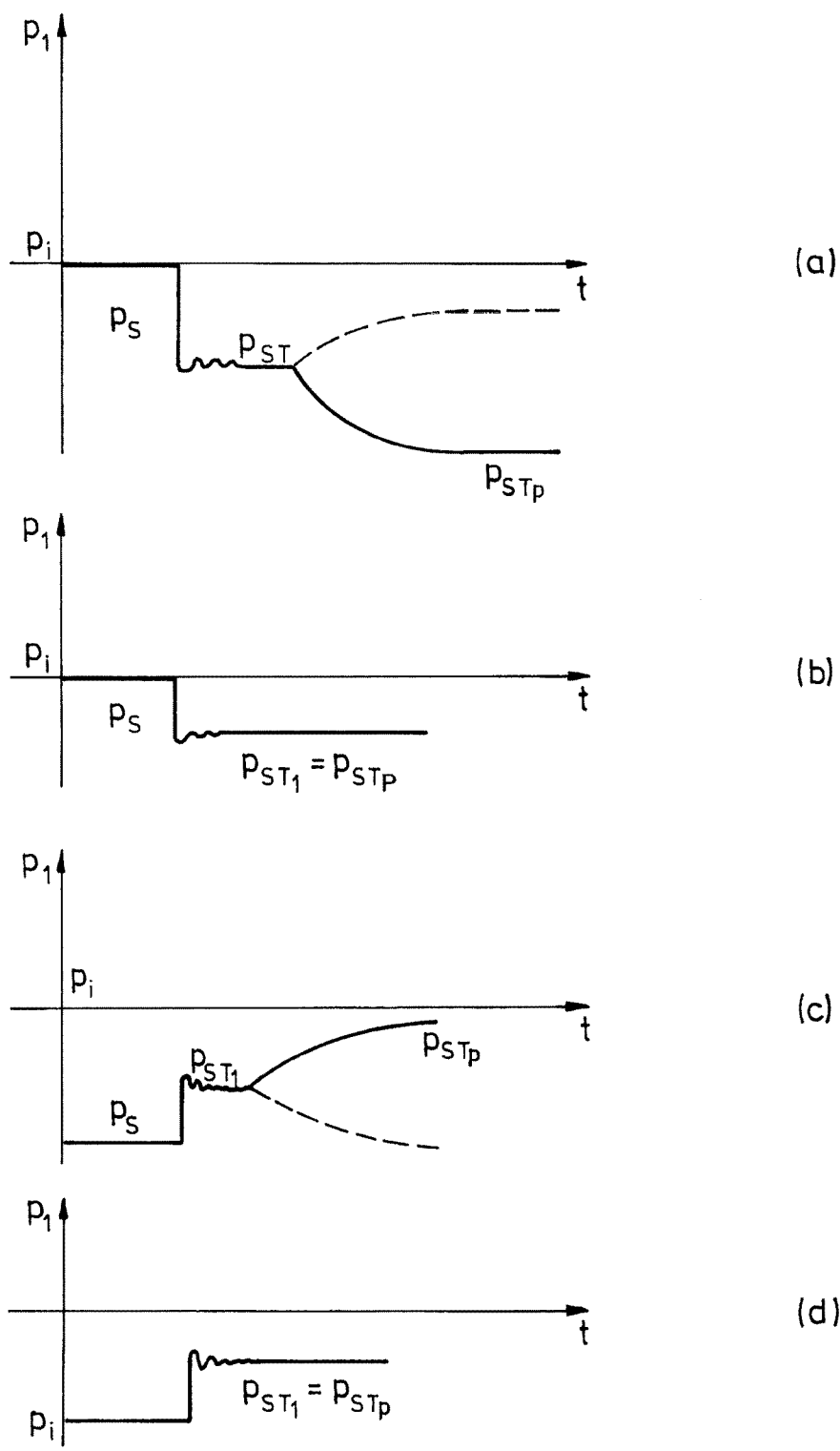
FIG. 2(a) to (d) Qualitatively, pressure courses as may be established and evaluated in a compartment by the present invention, FIG. 3 still in a qualitative representation in analogy to FIG. 2, a further course of pressure in a compartment as may be established and evaluated by the present invention, FIG. 4 simplified and schematically, one possibility according to the present invention, to establish a pressure step in a compartment, FIG. 5 in a representation in analogy to that of FIG. 4, a further possibility to establish a pressure step to a compartment, FIG. 6 by means of a simplified and schematic signal flow/functional block diagram and departing from an embodiment of the invention according to FIG. 1, a further development of that embodiment, FIG. 7 by means of a simplified signal flow/functional block diagram, an apparatus and method for providing reference signals to be applied to or to be generated by an embodiment of the present invention, FIG. 8 in a simplified and schematic signal flow/functional block diagram, a further embodiment of the apparatus according to the invention and operating the method according to the invention, FIG. 9 by means of a simplified and schematic signal flow/functional block diagram, an embodiment of the apparatus according to the invention, operating the method according to the invention and as today principally realized, FIG. 10 most simplified and schematically, an embodiment of the apparatus according to the invention and operation the method according to the invention, constructed principally according to the embodiment of FIG. 9 with a ceramic membrane capacitance pressure sensor and as used for providing measurements according to FIGS. 11 and 12, FIG. 11 a pressure step response including fTSR of He(a) and of AR(b), FIG. 12 the dependency of fTSR from one-dimensional extent variation of a tubular compartment.
Figure 3:
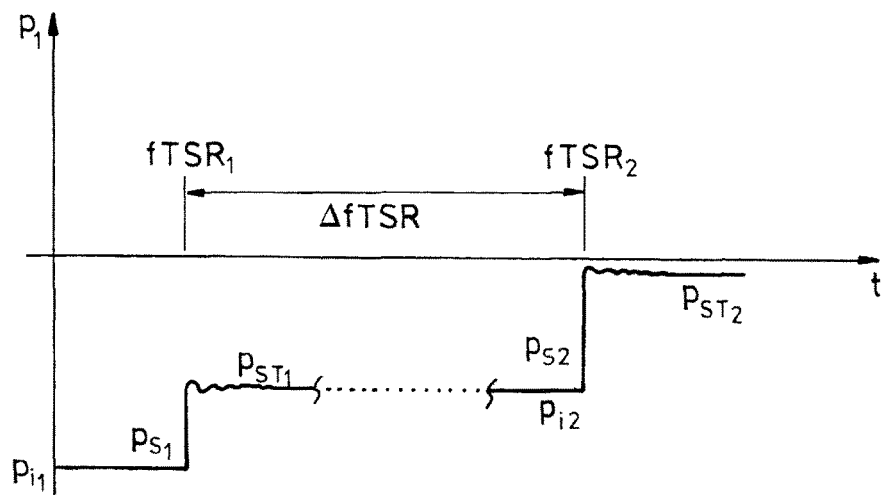

Applying a first and second and possibly even more pressure steps $p_{s1}$, $p_{s2}$ . . . may be performed in any combination of courses as exemplified in FIG. 2.

Figure 4:
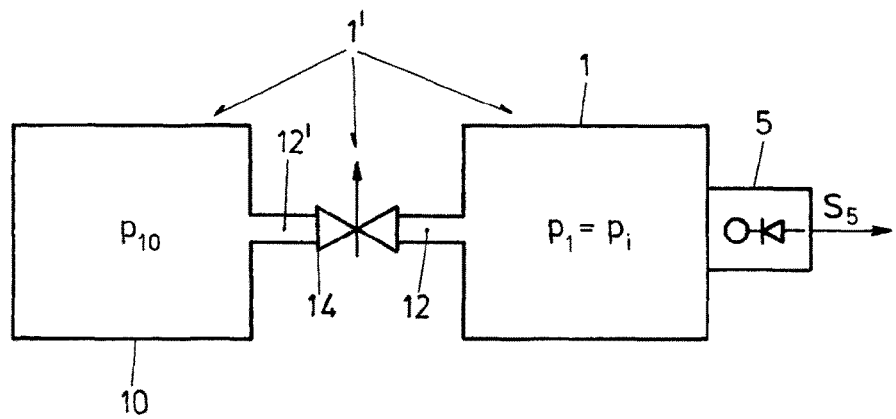

FIG. 4 shows schematically and by means of a simplified signal flow/functional block diagram one embodiment for realizing a pressure step source 3 as of FIG. 1.

According to FIG. 4 compartment 1 is in flow communication with a preload compartment 10 via a large flow communication line 12, 12' and a controllable valve member 14. With the closed valve 14 preload compartment 10 is loaded to a predetermined pressure $p_{10}$, which is different from the pressure $p_1$ prevailing in compartment 1.

The gas or gas mixture in preload compartment 10 is normally the same gas or gas mixture as present in compartment 1. By abruptly opening valve 14 the pressure $p_{10}$ and the pressure in compartment 1, $p_1$, become equal, which results in a pressure step $p_s$ in compartment 1 with pressure sensor 5. One may have to consider the geometry of the combined system of preload compartment 10, lines 12, 12', valve 14 and compartment 1 as co-determining the frequency fTSR. Thereby, it may be a good approach to in fact exploit such combined system as resulting compartment 1', wherein further processing is performed. Clearly, the pressure $p_{10}$ may be higher or lower than the pressure $p_i$, at least one of these pressures may be a vacuum pressure.

Figure 5:
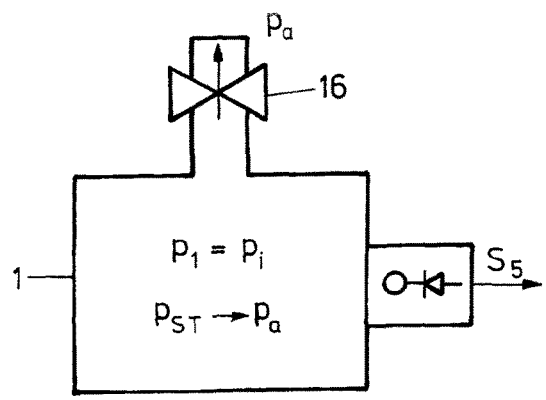

In a most straight ahead embodiment of the method and apparatus according to the invention and as shown in FIG. 5 the pressure step source is realized by discharging the pressure $p_1$ prevailing in compartment 1, by means of a controlled discharge valve arrangement 16 to ambient at ambient pressure $p_a$. Thereby, the pressure $p_1$ exploited for performing processing in compartment 1 is $p_i$ and the stationary step response pressure $p_{ST}$ is ambient pressure $p_a$.

Figure 6:
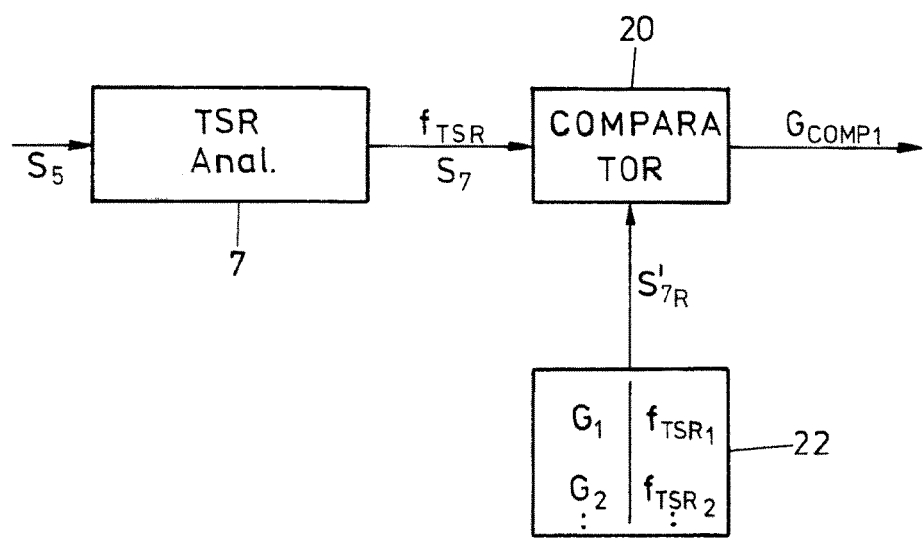

FIG. 6 shows by means of a simplified signal flow/ function block diagram an embodiment of further evaluating the output signal $S_7$, indicative for the fTSR of a gas or gas mixture prevailing in compartment 1, so as to quantitatively establish which gas or gas mixture is present in the compartment 1 at the instance of applying the pressure step $p_s$ or at least to which group of gases or gas mixtures the gas or gas mixture in compartment 1 belongs. The output signal of TSR analyzer unit 7, which is indicative for fTSR of the gas or gas mixture prevailing in compartment 1, is fed to a comparing unit 20.

In a reference signal unit 22, in the simplest way, there is stored a reference signal which is indicative for the fTSR of that gas or gas mixture which is expected to be present in compartment 1. The reference signal indicative for the reference fTSR of a gas or gas mixture expected to be in compartment 1, has been provided and stored by analyzing the step response of that expected gas, in fact a reference gas, substantially following the process according to FIG. 1.

Figure 7:
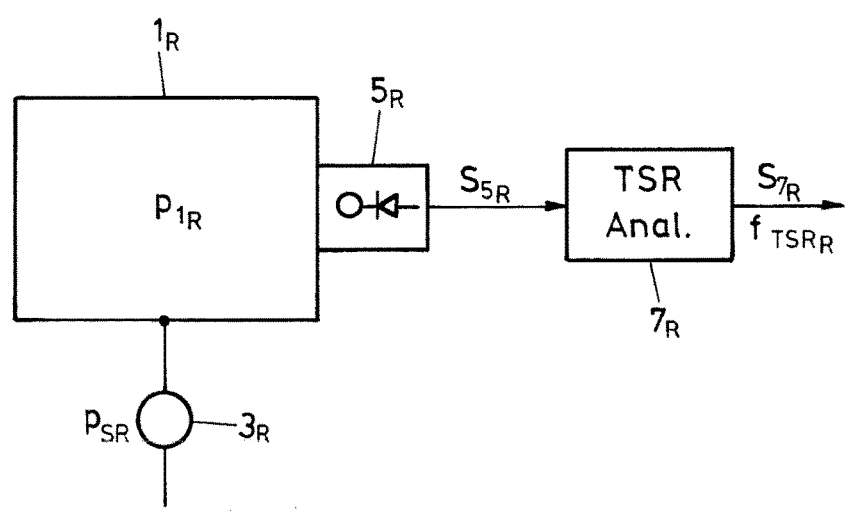

Thus and according to FIG. 7, a reference pressure step $p_{sR}$ is applied to a reference compartment $1_R$ by means of reference pressure step source $3_R$. The reference compartment $1_R$ is filled with that gas or gas mixture which is expected to be found in compartment 1. The pressure course and thereby especially the fTSR in reference container $1_R$ is monitored by the reference pressure sensor $5_R$. The output signal of the pressure sensor $5_R$, $S_{5R}$, is fed to a reference analyzer unit $7_R$, preferably operating equally to analyzer unit 7 of FIG. 1. The output signal $S_{7R}$ from the addressed TSR analyzer unit $7_R$ is indicative for the frequency fTSRR of the known gas or gas mixture in compartment $1_R$, which gas or gas mixture is expected to be present in compartment 1.

The following cases should be considered:

If the geometry of the inner space of compartment 1 and of reference compartment $1_R$ are different, then at least one of the signals $S_{7r}$ and of $S_7$ should be converted, so that fTSRR and fTSR to be in fact compared at comparator unit 20 refer to frequencies at equal geometries of the respective inner spaces.

If the initial pressure $p_i$ exploited for the pressure step in reference compartment $1_R$ is different from the initial pressure $p_i$ as exploited in compartment 1 and the difference of such initial pressures is relevant, again at least one of $S_{7R}$ and $S_7$ should be converted so that, at comparator unit 20, frequency comparison is performed with respect to frequencies established by step responses with equal initial pressures.

If the stationary step response pressure level as exploited in the reference compartment $1_R$ is different from the stationary step response level $p_{ST}$ as applied to compartment 1 and such difference is relevant with respect to fTSR, then again at least one of the output signals $S_7$ and $S_{7R}$ should be converted so as to ensure that at comparator unit 20 as of FIG. 6 a proper comparison is performed.

The same is valid if the pressure sensor 5 and the reference pressure sensor $5_R$ are different and possibly even if analyzing in analyzer unit 7 and in reference analyzer unit $7_R$ are different. Further, the same prevails if the gas temperature in reference compartment $1_R$ is different from the gas temperature in compartment 1 when applying the respective pressure step $p_s$ and $p_{SR}$.

A reference signal or more than one reference signals $S_{7R}$, indicative for the respective fTSRR of specific gas or gas mixtures, may be provided from a remote instance, e.g. from a server via online communication or may be provided on a storing unit as on a chip to be exploited when practicing the invention.

As shown in FIG. 6 the unit 22 may comprise a look-up table with two or more than two reference fTSRR representing signals, fTSR1, fTSR2 . . . fTSRn assigned to the respective gas or gas mixtures G1 . . . Gn.

Thereby and in such a case the prevailing fTSR indicative signal $S_7$ is compared in unit 20 with the reference frequency signals in the look-up table of unit 22. The comparator unit outputs a gas or gas species indicative signal $G_{COMP1}$ indicative for that gas or gas mixture $G_1, \ldots G_n$ out of look-up table in unit 22, the reference fTSRR signal $s_{7R}$ fitting best with the fTSR-representing signal S7. Please note that similar fTSR may be indicative for a group of gases or gas mixtures rather than for specific gases or gas mixtures.

Figure 8:
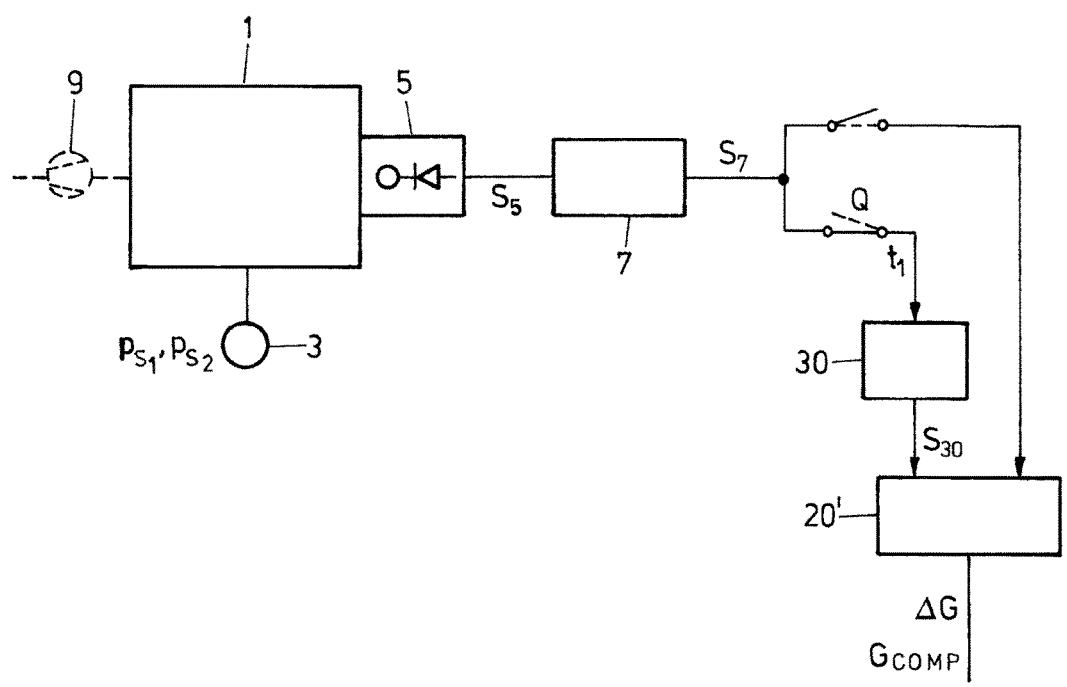

FIG. 8 shows in a simplified and schematic signal flow/functional block diagram a further embodiment of the method and apparatus according to the invention. Here, the compartment 1 is loaded by at least two pressure steps from pressure step source 3 staggered in time as e.g. shown in FIG. 3. The fTSR—representing signal S7 resulting from the first pressure step $p_{s1}$ is stored in a storing unit 30 at time $t_1$, at which the first pressure step $p_{s1}$ is applied.

As shown schematically by the switches Q in FIG. 8, at the occurrence of the second pressure $p_{s2}$ the signal $S_7$ representing the fTSR resulting from the second pressure step $p_{s2}$ is fed to comparator unit 20', together with the signal $S_{30}$ according to the signal stored in storage unit 30, which accords to the fTSR signal as caused by the first pressure step $p_{s1}$.

The following considerations prevail:

If it is intended to just monitor a difference of gas or gas mixtures prevailing in compartment 1 at the instances of applying $p_{s1}$ and $p_{s2}$, the output signal of comparator unit 20' is just indicative of a gas or gas mixture difference ΔG, as none of the gases or gas mixtures prevailing in compartment 1 is known.

If, when the first pressure step $p_{s1}$ applied, the gas or gas mixture in compartment is known, then the output signal of comparator unit 20' is significant for approving or non-approving that the gas or gas mixture at the instance $p_{s2}$ is applied, is or not equal to the addressed known gas or gas mixture. In fact, if at the instance the first pressure step $p_{s1}$ is applied to compartment 1, the gas or gas mixture contained therein is exactly known, then storing unit 30 becomes the reference signal unit 22 as of FIG. 6. In the embodiment of FIG. 8 the geometry of the inner spaces of the reference compartment is equal to the geometry of the inner space of compartment 1, because compartment 1 is exploited as reference compartment. Further, it is evident that in this case the reference pressure sensor $5_R$ and the pressure sensor 5, the analyzer unit $7_R$ and the analyzer unit 7 are equal.

Figure 9:
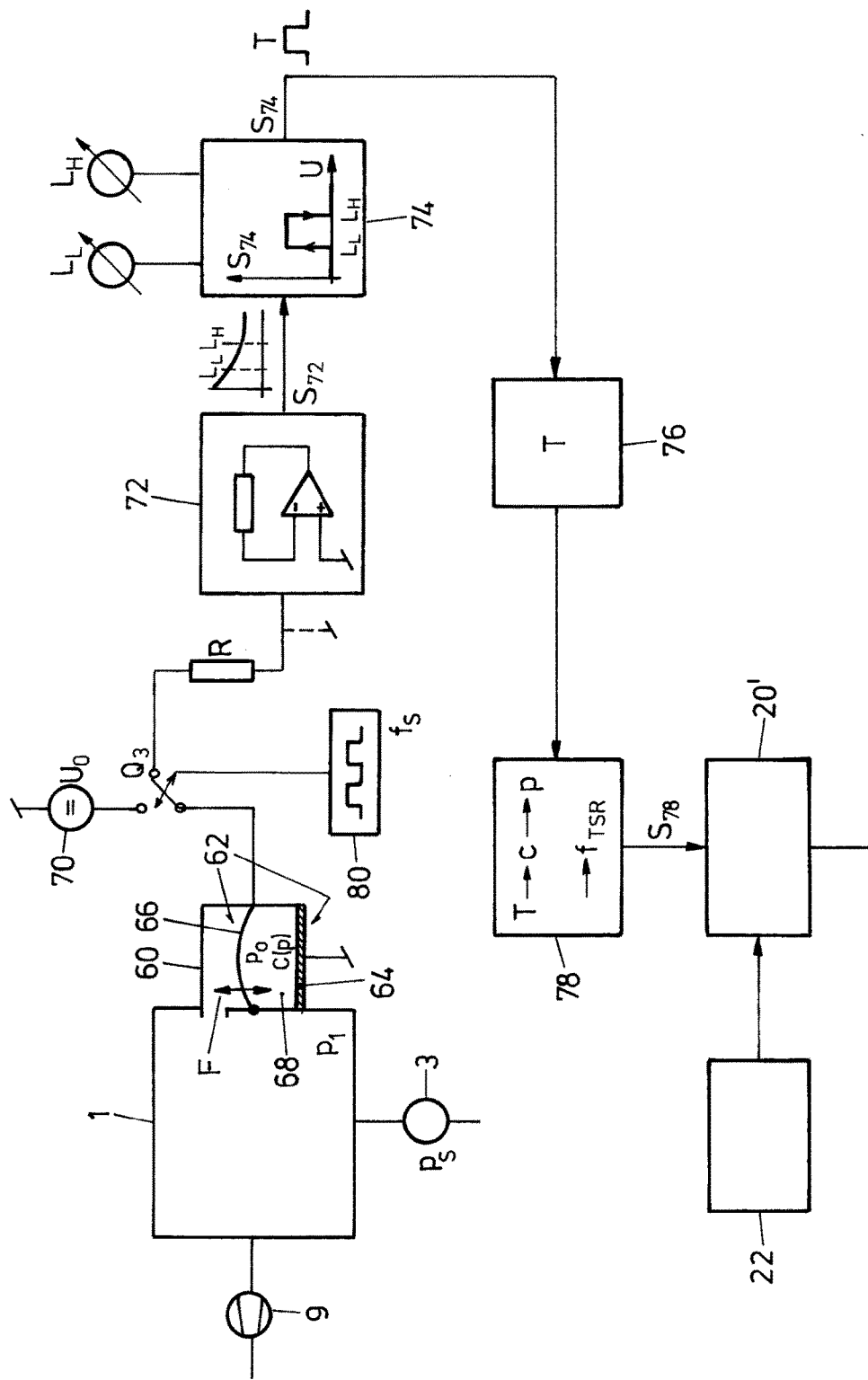

FIG. 9 shows in a simplified and schematic signal flow/functional block diagram an embodiment of the method and apparatus according to the present invention and as today practiced, wherein exploiting a capacitance pressure sensor and a sampling technique are combined.

According to FIG. 9 the pressure course $p_1$ within compartment 1 is sensed by means of a capacitance pressure sensor 60. As schematically shown, such capacitance pressure sensor comprises a capacitor 62, the capacity thereof being dependent on the pressure $p_1$ as sensed.

The capacitor 62 comprises, as an example, a rigid electrode 64 and, as a second electrode, a membrane 66. One side of membrane 66 is exposed to a reference pressure $p_o$ within an interspace between the electrodes 64 and 66. The second surface of membrane 66 is exposed, as schematically shown in FIG. 9, to the inner space of compartment 1.

As a function of pressure difference between pressure to be sensed and reference pressure $p_o$ the membrane electrode 66 is deformed, e.g. bowing more or less out towards the lower of the addressed two pressures $p_o$ and $p_1$ and as schematically shown by the double arrow F in FIG. 9.

Thereby, the capacity C(p) of the capacitor 62 varies dependent from the pressure to be sensed in compartment 1. The capacitor 62 is intermittently charged to a voltage $U_o$ of a source 70, as schematically represented, by closing a switch $Q_3$. Charging the capacitor 62 occurs very fast, as there is practically no resistivity limiting charging current.

After having charged the capacitor 62, the capacitor 62 is discharged via a resistive element R of accurately known resistivity value. According to FIG. 9 this is represented by switching the switch $Q_3$ to one tap of resistive element R, for illustrating purpose only shown as a resistor. Generically spoken, the time course of the discharge process of capacitor 62 is exclusively governed by C(p) and the resistivity valve of R. As shown in FIG. 9 a timespan T significant for the discharge characteristics is measured. Because the resistivity value of R is known, the momentarily prevailing capacity value of capacitor 62 may be calculated from the addressed time span T as measured, which capacity value is indicative for the pressure prevailing in compartment 1. According to FIG. 9 and as example the electrode 64 of capacitor 62 is operated on a reference electric potential, as e.g. on ground potential, whereas the second "tap" of resistive element R is operated virtually on the addressed reference potential as well, in that it is applied to the inverting input of an operational amplifier unit 72. The positive input to the amplifier unit 72 is operated on reference potential as well. Thus, at the output of amplifier unit 72 and depending on the amplification set at the amplifier unit 72, a signal $s_{72}$ is generated, picturing the discharge current of capacitor 62 through resistive element R. The output signal of amplifier unit 72 is input to a comparator unit 74, comprising e.g. a Schmidt Trigger. At the comparator unit 74 there is set a first voltage level $L_L$ for input signal $S_{72}$, at which the output $s_{74}$ of the comparator unit 74 jumps from a first state to a second state, and a second level $L_H$ for input signal $S_{72}$, at which the output $S_{74}$ of comparator unit 74 jumps back to the first state. The levels $L_L$ and $L_H$ are set according to subsequent voltage levels passed by the discharge indicative signal $S_{72}$, as capacitor 62 is discharged via resistive element R. E.g. the two levels may be set so, that the timespan the discharge process needs to pass from $L_L$ to $L_H$ accords with the momentarily prevailing time constant T=C(p)·RΩ, whereas RΩ denotes the resistivity value of element R.

The output signal $S_{74}$ and thereby specifically the time extent T of the output pulse is significant for the momentarily prevailing capacity value of capacitor 62. In a time measuring unit 76 a highly accurate measurement of the timespan T is performed and, based on the known characteristic of the capacitance pressure sensor, i.e. the known dependency of C(p) from pressure p, the pressure momentarily prevailing in compartment 1 is calculated in an analyzer unit 78. Charging/discharging capacitor 62 is controlled, as schematically shown by switch $Q_3$, by means of a clock unit 80. Given a range of expected fTSR to be evaluated, charging and discharging of the capacitor 62 is performed at a repetition or sampling frequency $f_s$, which is at least twice the highest fTSR expected. In a good embodiment the sampling frequency $f_s$ is at least 5 times, in an even better embodiment at least 10 times, higher than the addressed highest expected fTSR. The sampling frequency $f_s$ is to now selected to be at least 0.5 kHz and even better to be at least 5 kHz. Thus, by the addressed sensing technique the pressure course in compartment 1 is sampled at a respectively high sampling frequency. At the output of comparator unit 74 a pulse train is generated at the addressed charging and discharging sampling frequency $f_s$, controlled by clock unit 80. The analyzer unit 78 in fact performs time to capacity to pressure to fTSR conversion and generates an output signal $S_{78}$, which is evaluated in a comparator unit 20' as was explained in context with FIG. 6.

Very accurate and highspeed measurement of the timespan T or more generically of a timespan significant for the discharging process of capacitor 62 through resistive element R is performed by constructing the time measuring unit 76 as a Time to Digital Converter (TDC). Especially in this case subsequent signal processing as by unit 78 and comparing unit 20' is performed digitally, e.g. by Digital Signal Processing unit e.g. realized by an ASIC.

Figure 10:
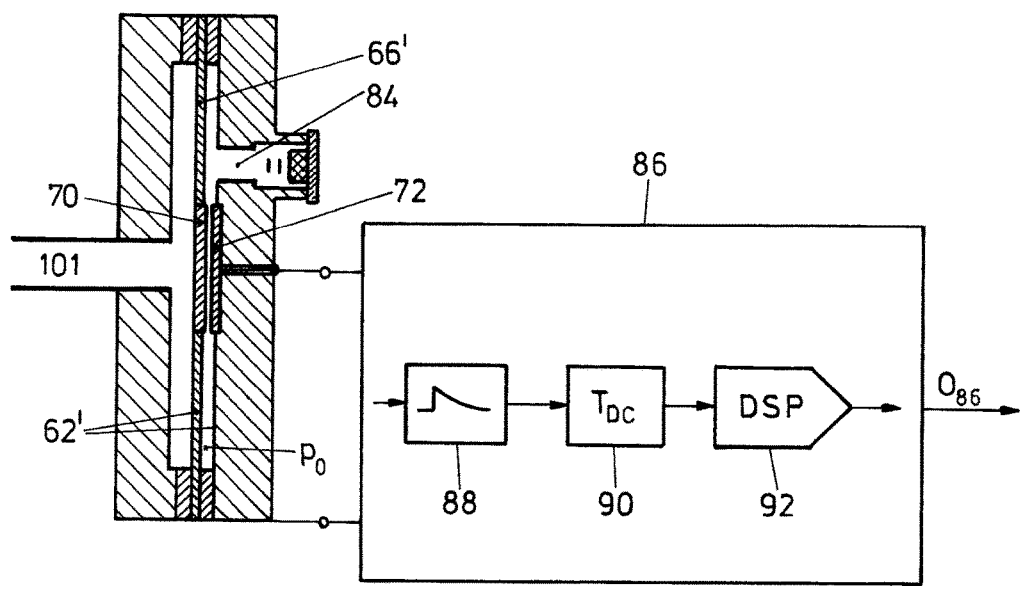

FIG. 10 shows schematically and simplified that part of the apparatus according to the present invention and operating the method of the invention, by which the prevailing pressure course in compartment 1 as of FIG. 9 is measured and monitored. As a capacitor pressure sensor a sensor as amply disclosed in the WO 2007/019714 to the same applicant as the present invention is used. Therein, the capacitor 62', the capacity of which being dependent on the pressure to be sensed, is formed by a membrane 66' of a ceramic material as of $Al_2O_3$ and comprises an electroconductive layer as of a metal 70. The second electrode of capacitor 62' is formed by a rigid electroconductive element 72 as of a metal. The sealed interspace 84 between the electrode 66', 72, is the reference pressure chamber according to compartment 68 of FIG. 9 and is loaded to a predetermined constant pressure $p_o$. The surface of membrane 66' opposite interspace 84 is in flow communication with the compartment 1 according to FIG. 9. The capacitor 62' is electrically tapped off and connected to a unit 86, wherein charging and discharging operation following the principles as explained in context with FIG. 9 is performed at a sampling unit 88, the discharge timespan is measured by a Time to Digital Converter unit 90 according to the time measurement unit 76 of FIG. 9. The time to pressure conversion and signal analysis is performed by a digital signal processing (DSP) unit 92.

The signal output at output $O_{86}$ accords with the sampled pressure course prevailing in compartment 1 and includes the transient step response with the respective oscillation at fTSR. It is this output signal which is further exploited, preferably by comparing with one or more than one reference fTSR signals as was explained in context with FIG. 6.

Figure 11:
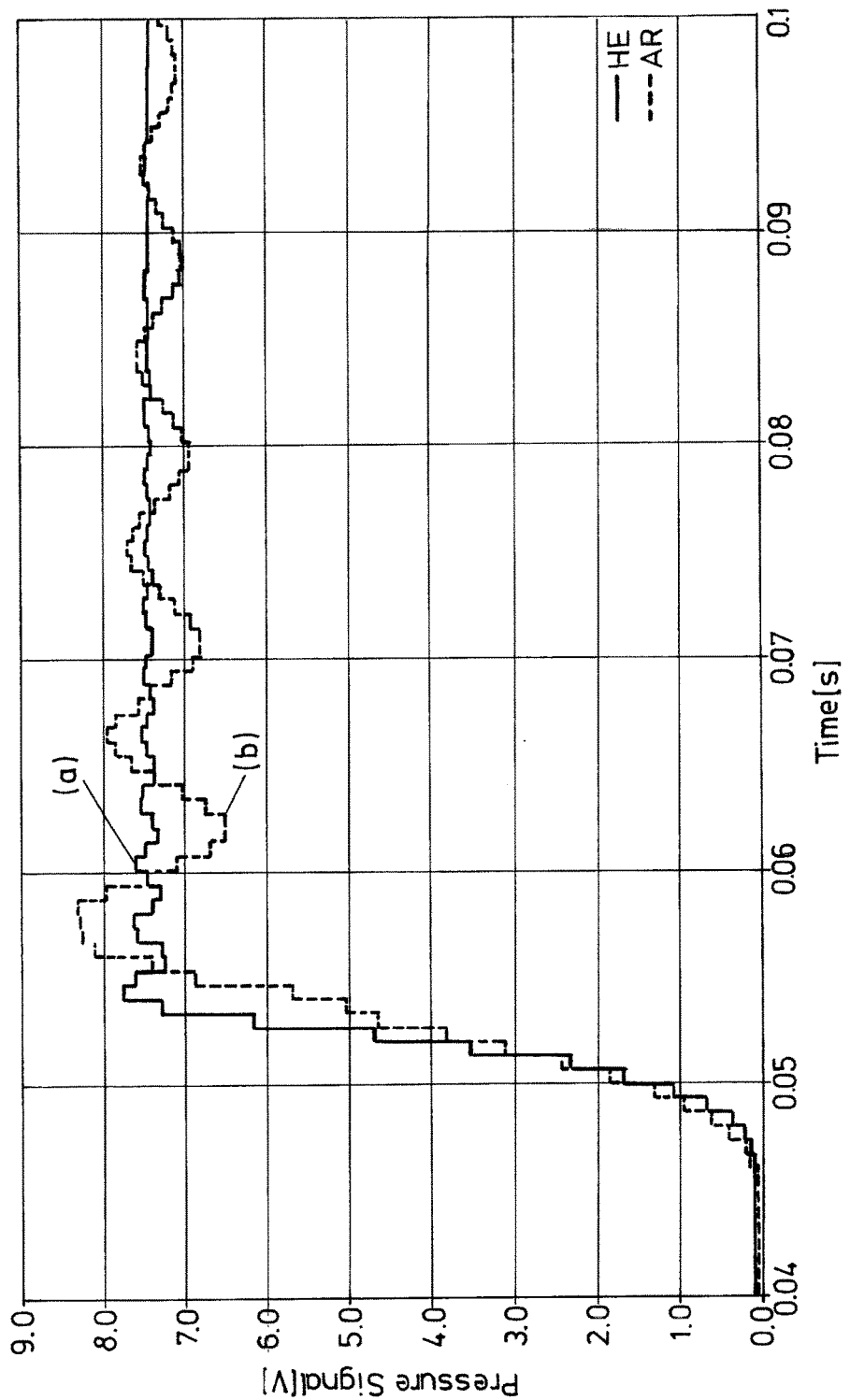

In a compartment 1 filled with Helium a pressure step from 5 Torr to 750 Torr was applied by floating compartment 1. The resulting transient step response (a) including transient step response oscillation is shown in FIG. 11. The transient response signal for Helium is denoted in FIG. 11 by (a), with the respective fTSR.

Then, with the same compartment 1 at the same temperature the same experiment was done with argon. The course (b) is the result signal at $O_{86}$, indicative for the resulting fTSR. The fTSR for Helium is about 0.3 kHz. The fTSR for Argon is about 0.1 kHz.

The sampling frequency $f_s$ is about 1.5 kHz.

As may be seen by evaluating the respective transient step response oscillation frequencies fTSR, which are specific for a gas or gas mixture prevailing in compartment 1, either the gas or gas mixture prevailing in that compartment or a change of gas or gas mixture occurring in that compartment may be monitored. According to the present invention the same pressure sensor is exploited on one hand to monitor the average or stationary pressure level in compartment 1 as is exploited for practical processing in compartment 1 as well as the transient pressure step response indicative for a gas or gas mixture prevailing in compartment 1 when a pressure step is applied.

With an eye on the charge/discharge sampling as exemplified in context with FIG. 9 it is perfectly clear to the skilled artisan that instead of monitoring the discharge process or additionally thereto, the charging process of capacitor 62 through a respective resistive element acting in analogy to R may be monitored.

Figure 12:
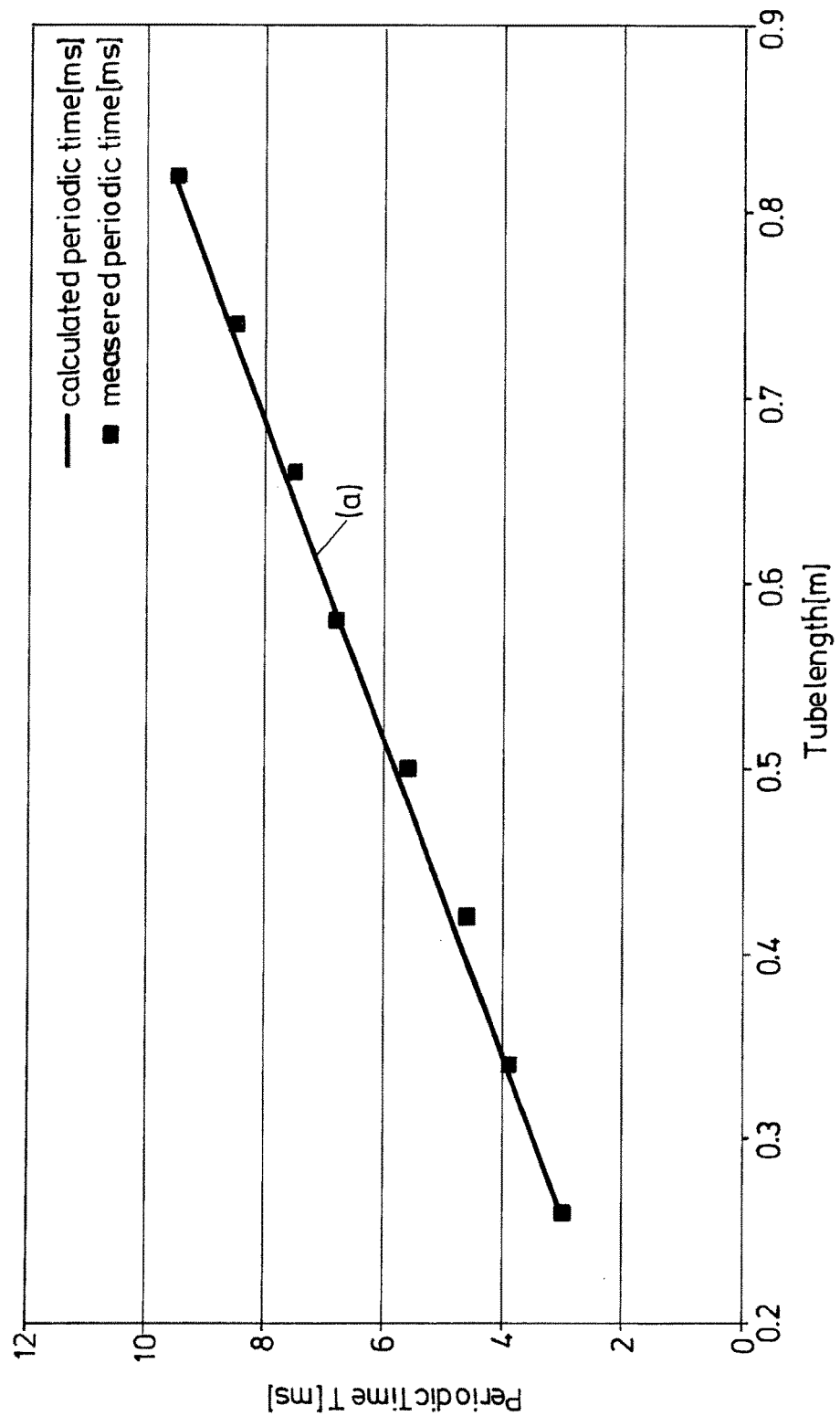

In FIG. 12 the influence of the geometry of compartment 1 on the resulting fTSR is shown. The compartment 1 was realized by a tube of constant inner cross-section. The length of that tube was varied. By means of the arrangement as disclosed and explained in context with the FIGS. 9 and 10 the fTSR was monitored at equal gases, equal pressures and equal pressure steps. It may be seen that the calculated fTSR, line (a), do accurately fit with the measured fTSR according to the measured oscillation periods. This experiment shows that it is absolutely possible to convert a fTSR measured in one compartment of one geometry of its inner space to a respective fTSR as would be measured at a differing geometry of the addressed inner space.

The invention claimed is:

1. A method of measuring pressure of a gas or gas mixture in a compartment defining an interior volume the method comprising: measuring said pressure by a pressure sensor, applying, by an external pressure change device, to said compartment at least one step of pressure, and measuring by said pressure sensor the transient step response oscillation frequency of the pressure in said compartment to the applied pressure step as indicative of an identity of the gas or gas mixture in said compartment, wherein said sensor being configured to automatically measure for an interval longer than an interval of the transient step response, wherein the identity of the gas or gas mixture is determined based on: a measured pressure, pi within the interior volume when the at least one step of pressure initiates, a measured pressure within the interior volume when the at least one step of pressure terminates, and a measured temperature within the interior volume during the at least one step of pressure: and wherein the measured pressure within the interior volume when the at least one step of pressure terminates is used by a processor determining the identity of the gas or gas mixture as the measured pressure when a subsequent step of pressure is initiated.

2. The method of claim 1, wherein said applying of said at least one step of pressure comprises applying a pressure step from ambient pressure to a target pressure.

3. The method of claim 1, wherein said applying of said at least one step of pressure comprises applying a pressure step from a pressure in said compartment to ambient pressure.

4. The method of claim 1, comprising applying said pressure step by abruptly expanding a gas from said compartment or into said compartment.

5. The method of claim 1, monitoring said frequency in time domain or in frequency domain.

6. The method of claim 1, comprising providing at least one reference transient step response oscillation frequency—fTSR—signal indicative for a fTRS of at least one gas or gas mixture and comparing a signal dependent from said fTSR monitored with a said reference fTRS signal.

7. The method of claim 6, comprising providing a multitude of gas or gas mixture specific reference fTSR signals preferably in form of a look-up table and comparing said signal dependent from said fTRS as monitored by said pressure sensor with said reference fTSR signals thereby outputting a gas or gas mixture indicative signal for that specific gas or gas mixture, the reference fTSR signal thereof fitting best with said signal dependent from said fTSR as monitored.

8. The method of claim 1, comprising providing said at least one reference fTSR signal by providing a reference compartment of predetermined geometry of inner space, applying to said reference compartment at least one reference step of pressure, monitoring by a further pressure sensor the resulting fTSR and storing a signal dependent from said resulting fTSR in said reference compartment as said reference fTSR signal.

9. The method of claim 8, wherein said dependent signal stored is derived from said fTSR as a function of at least one of
 a difference of predetermined geometry of said compartment and of said reference compartment, if existing and not neglectable,
 a difference of pressure level at which said fTSR in said reference compartment and in said compartment are monitored, if existing and relevant,
 a difference of temperatures at which said fTSR in said reference compartment and in said compartment are monitored, if existing and not neglectable.

10. The method of claim 9, wherein there is valid: said geometry of said reference compartment is equal to the said geometry of said compartment or said reference compartment is said compartment.

11. The method of claim 8, comprising deriving said signal dependent from said fTSR monitored as a function of at least one of
 a difference of predetermined geometry of said compartment and of said reference compartment, if existing and not neglectable,
 a difference of pressure level at which said fTSR in said reference compartment and in said compartment are monitored, if existing and not neglectable,
 a difference of temperatures at which said fTSR in said reference compartment and in said compartment are monitored, if existing and not neglectable.

12. The method of claim 8, wherein there is valid: said further pressure sensor is equal to said pressure sensor or said further pressure sensor is said pressure sensor.

13. The method of claim 8, wherein there is valid at least one of:
 said step of said reference pressure is equal to said step of pressure,
 the pressure level in said reference compartment before said reference step is applied is equal to the pressure level in said compartment before said step is applied,
 the stationary pressure level in said reference compartment before said reference step is applied is equal to the stationary pressure level in said compartment before said step is applied,
 the stationary pressure level in said reference compartment after said reference step is applied is equal to the stationer pressure level in said compartment after said step is applied,
 the temperature in said reference compartment during applying said reference step is equal to the temperature in said compartment during said step being applied.

14. The method of claim 1, wherein at least said monitoring by said sensor comprises sampling a signal dependent from an output signal of said sensor at a sampling frequency which is at least 5 times higher than said fTSR, said sampling frequency being at least 0.5 kHz.

15. The method of claim 1, wherein said measuring and said monitoring by said pressure sensor comprises:
 providing a pressure sensing capacitor with two electrodes, the capacity of said capacitor being dependent from said pressure in said compartment,
 electrically monitoring the course of said capacity of said capacitor.

16. The method of claim 15, thereby monitoring said course of said capacity by sampling, each sampling comprising:
 charging and discharging said capacitor, thereby performing at least one of said charging and of said discharging of said capacitor via a resistive element of predetermined resistivity, which, together with said capacity being decisive for the time course of said at least one of charging and of discharging, and measuring a time span during said at least one of charging and of discharging said capacitor between a first predetermined charging level and a second different predetermined charging level.

17. The method of claim 16, said measuring of said time span being performed by Time to Digital Conversion (TDC).

18. The method of claim 15, wherein one of said electrodes comprises a ceramic material membrane, preferably made of $Al_2O_3$.

19. The method of claim 1, comprising digital signal processing.

20. An apparatus for measuring pressure in a compartment exposed to a pressure step change from an external pressure change device, comprising: a sensor measuring an averaged pressure level in said compartment, averaged over a predetermined time span, and generating a respective pressure level indicative signal; the sensor measuring a transient pressure step response oscillation frequency of the pressure in said compartment fTSR to the applied pressure step; processor for evaluating said fTSR to identify a gas or gas mixture disposed within the compartment, wherein the identity of the gas or gas mixture is determined based on: a measured pressure, $p_i$ within an interior volume of the compartment when the at least one step of pressure initiates, a measured pressure within the interior volume when the at least one step of pressure terminates, and a measured temperature within the interior volume during the at least one step of pressure; and wherein the measured pressure within the interior volume when the at least one step of pressure terminates is used by the processor identifying the gas or gas mixture as the measured pressure when the a subsequent step of pressure initiates.

21. The apparatus of claim 20, said sensor measuring an average pressure level and said sensor monitoring transient pressure step comprise a shared capacitance pressure sensor, with a capacitor, the capacity thereof being dependent from an input pressure to be sensed and charging/discharging means for charging and discharging said capacitor, thereby at least one of charging and of discharging being performed through a resistive element, the resistivity value thereof defining together with the capacity value of said capacitor, the course of said at least one of charging and of discharging, and time measuring means for measuring a time span, characteristic of said at least one of said charging and of said discharging through said resistive element.

22. The apparatus of claim 21, comprising a clock unit, controlling said charging and discharging at a repetition frequency which is at least 5 times, preferably at least 10 times higher than an expected fTSR, said repetition also called sampling frequency being preferably at least 0.5 kHz, more preferred at least 5 kHz.

23. The apparatus of claim 21, said time measuring means comprising a Time to Digital Converter.

24. The apparatus of claim 21, wherein said sensor measuring an average pressure level and said sensor monitoring transient pressure step comprise a shared capacitor pressure sensor with a capacitor, the capacity thereof being dependent from an input pressure, said capacitor comprising a membrane electrode of a ceramic material, preferably made of $Al_2O_3$.

25. The apparatus of claim 21, wherein said processor comprises comparing means for comparing a signal representing said fTSR with a signal representing a reference fTSR.

26. The apparatus of claim 20 said processor comprising a digital signal processing unit.

27. The apparatus of claim 20, said sensor measuring an average pressure level and said sensor monitoring transient pressure step comprise a shared pressure sensor and at least said sensor monitoring transient pressure step comprising sampling means for sampling the output signal of said shared pressure sensor at a sampling frequency which is at least 5 times higher than an expected fTSR, said sampling frequency is at least 0.5 kHz.

28. The apparatus of claim 20, wherein said processor means comprises a look up table with a multitude of signals representing gas or gas mixture identifying reference fTSR and said comparing means being adapted for comparing a signal representing said fTSR with said multitude of signals representing said identifying reference fTSR and further being adapted to output an output signal identifying at least one specific gas or gas mixture, the signal representing said reference fTSR of said at least one specific gas or gas mixture fitting best with said signal representing said fTSR.

* * * * *